United States Patent [19]

Bracke et al.

[11] Patent Number: 4,517,295

[45] Date of Patent: May 14, 1985

[54] HYALURONIC ACID FROM BACTERIAL CULTURE

[75] Inventors: James W. Bracke, Minnetonka; Kipling Thacker, Minneapolis, both of Minn.

[73] Assignee: Diagnostic, Inc., Minneapolis, Minn.

[21] Appl. No.: 467,925

[22] Filed: Feb. 18, 1983

[51] Int. Cl.$^3$ .................. C12P 19/04; C12R 1/46
[52] U.S. Cl. .................. 435/101; 435/801; 435/885; 536/55.1; 536/123
[58] Field of Search .............. 435/101, 801; 536/55.1, 536/123

[56] References Cited

U.S. PATENT DOCUMENTS

| | | | |
|---|---|---|---|
| 2,975,104 | 3/1961 | Warren | 435/101 |
| 4,141,973 | 2/1979 | Balazs | 424/180 |
| 4,303,676 | 12/1981 | Balazs | 424/359 |
| 4,328,803 | 5/1982 | Pape | 424/180 |
| 4,393,136 | 7/1983 | Cheetham | 435/161 |

FOREIGN PATENT DOCUMENTS

| | | |
|---|---|---|
| 183707 | 11/1982 | Japan . |
| 212300 | 12/1982 | Japan . |
| 56692 | 4/1983 | Japan . |
| 57319 | 4/1983 | Japan . |
| 1557755 | 12/1979 | United Kingdom . |
| 950735 | 8/1982 | U.S.S.R. . |

OTHER PUBLICATIONS

Van De Rijn et al., Infection and Immunity, vol. 27, No. 2, pp. 444-448, (Feb. 1980).
Merck Index 9th Edition 1976 entry, 4634—"Hyaluronic Acid".
"Isolation of Hyaluronic Acid from Cultures of Streptococci in a Chemically Defined Medium," *Acta Path. Microbiol. Scand,* Sect. B, 84:162-164, 1976.
Cumulated Index Medicus, 1980 (three pages) Specifically Hyaluronic Acid Entry, p. 1; Biosynthesis, p. 2 and Biosynthesis p. 3.
"The Biosynthesis of Hyaluronate by Group A Streptococci," Yael Gintzburg, a 1955 Thesis at the University of Minnesota.
"The Biosynthesis of Hyaluronic Acid by Group A Streptococcus," *Journal of BioChemistry,* 1953, Roseman, Saul et al., pp. 213, 224, 225.
"The Effect of Diflunisal on Hyaluronic Acid Production by 'Activated' Human Snovial Fibroblasts," *Br. J. Clin. Pharmac.* (1981), 12, 423-426 by Michael Yaron and Ilana Yaron.
"Biosynthesis of Proteo Glycans and Hyaluronate in Human Fibroblast Cultures Established from Normal and Pathological Corneas," *Exp. Eye Res.,* 1981, 32, 435-443, by Inger Marie Dahl.
"Biosynthesis of Polysaccharides by Prokaryotes," *Ann Rev. Microbiol,* 1979, 33:169-199, by Sheri J. Tonn and J. E. Gander.
"Effect of Cycloheximide and Dexamethasome Phosphate on Hyaluronic Acid Synthesis and Secretion in Cultured Human Skin Fibroblasts," *Journal of Cellular Physiology,* 109:215-222, (1981), by J. L. Mapleson and M. Buchwald.
"Hyaluronic Acid and Hyaluronaise Produced by 78 Hemolytic Streptococci, Comprising 40 Types of Group A$^1$ (Table 1)," *Acta. Pathol. Micro. Scand.* 35, (1954), 159-164, by V. Faber and K. Rosendal.
"The Biosynthesis of Hyaluronic Acid," *Chem. Mol. Biol. of the Intercell,* Matrix 2, E. A. Balazs (Ed.) 1970, by Bernard Jacobson, pp. 763-781.
"The Biosynthesis of Hyaluronic Acid in Group A Streptococci," *Chem. Mol. Biol. of the Intercell,* Matrix 2, pp. 783-794, E. A. Balazs (Ed.) 1970, by Stoolmiller and Dorfman.
"Type IIA Hyperlipoproteinemic Sera Decrease the Synthesis of Hyaluronic Acid by Cultured Human Aortic Smooth Muscle Cells," *Atherosclerosis,* 39, (1981), 61-69, by Jarvelainen, Ronnemaa et al.
"The Synovial Fluid Hyaluronic Acid in Rheumatoid Arthritis", *Experimentia,* 34 (12): p. 1545, (1978), by J. A. Kofoed.
"Abnormalities of Connective Tissue Cells Cultured from Patients with Rheumatoid Arthritis" from Department of Internal Medicine, and the Rackham Arthritis Research Unit, The University of Michigan Medical School, Ann Arbor, Michigan, pp. 65-75.
"Preparation and Stability of Hyaluronic Acid" *Biochem. Biophys. Acta.,* 53, (1961), 254-262, by Ward Pigman et al.
"Studies on Hyaluronic Acid I. The Preparation and Properties of Rooster Comb Hyaluronic Acid," *Biochimica et Biophysica Acta,* 156, (1968), 17-30, by David A. Swann.
"The Hydrolysis of the Polysaccharide Acids of Vitreous Humor, of Umbilical Cord, and of Streptociccus of the Autolytic Enzyme of Pneumococcus", J.B.C. 118, (1937), pp. 71-78, by Karl Meyer.

(List continued on next page.)

*Primary Examiner*—Lionel M. Shapiro
*Attorney, Agent, or Firm*—Schroeder, Siegfried, Vidas & Arrett

[57] ABSTRACT

Hyaluronic acid, a polysaccharide, is prepared in high yield from streptococcus bacteria by fermenting the bacteria under anaerobic conditions in a $CO_2$-enriched growth medium, separating the bacteria from the resulting broth and isolating the hyaluronic acid from the remaining constituents of the broth. The bacteria may be grown free of endotoxins by filtering all ingredients through a 10K Millipore ® filter prior to inoculation of the medium and subsequently maintaining pyrogen-free conditions. Separation of the microorganisms from the polysaccharide is facilitated by killing the bacteria with trichloroacetic acid. After removal of the bacterial cells and concentration of the higher molecular weight fermentation products, the hyaluronic acid is isolated and purified by precipitation, resuspension and reprecipitation.

30 Claims, No Drawings

OTHER PUBLICATIONS

Abstract Entitled, "Hyaluronic Acid Capsule; Strategy for Oxygen Resistance in Group A Streptococci," *Chemical Abstracts*, vol. 92, Abstract 90592w, 1980, p. 274 by Cleary P. Patrick.

Abstract entitled, "The Mechanism of Estrogen-Induced Increase in Hyaluronic Acid Biosynthesis, with Special Reference to Estrogen Receptor in the Mouse Skin," *Chemical Abstracts*, vol. 92, Abstract 88269c, 1980, by Makoto Usuka, pp. 63, 64.

Abstract entitled, "Effects of Sodium Aurothiomalate on Hyaluronic Acid Synthesis in Normal and Rheumatoid Synovial Fibroblast Cultures," *Chemical Abstracts*, vol. 92, 1980, by Eero Vuorio et al., p. 54, Abstract 33945q.

"Cell-Free Synthesis of Hyaluronic Acid in Marfan Syndrome," *Journal of Biological Chemistry*, (1979), pp. 12199–12203.

"Biosynthesis of Proteoglycans and Hyaluronate in Rabbit Corneal Fibroblast Cultures, Variation with Age of the Cell Line and Effect of Foetal Calf Serum," *Exp. Eye Res.*, (1981) 32, 419–423, by Inger Marie Dahl.

"The Role of Glutamine in the Biosynthesis of Hyaluronate by Streptococcal Suspensions," *Biochemical Journal*, vol. 62, (1956), by D. A. Lowther et al., pp. 304–314.

"The Capsulation of Streptococci and its Relation to Diffusion Factor (Hyaluronidase)", *Journal of Pathology and Bacteriology*, vol. 53, (1941), pp. 13–27, by Douglas McClean.

"Hyaluronate Capsule Prevents Attachment of Group A Streptococci to Mouse Peritoneal Macrophages," *Infection and Immunity*, Mar. 1981, pp. 985–991, by Ellen Whitnack et al.

"The Biosynthesis of Hyaluronic Acid by Group A Streptococcus VI. Biosynthesis from Uridine Nucleotides in Cell-Free Extracts," *The Journal of Biological Chemistry*, vol. 234, No. 9, pp. 2343 and 2350, Sep. 1959, by Alvin Markovitz et al.

"The Biosynthesis of Hyaluronic Acid by Group A Streptococcus V. The Uridine Nucleotides of Group A Streptococcus," *The Journal of Biological Chemistry*, (1957), 228: 547–557, by J. A. Cifonelli.

"Hyaluronic Acid—Chapter 2," *Carbohydrates of Living Tissue*, by M. Stacey et al., (1962), pp. 37–58.

"A Method for the Purification of Bovine Vitreous Body Hyaluronic Acid" *Biochimica et Biophysica Acta* 673, (1981), 192–196, by Otto Schmut et al.

"Structure of Hyaluronic Acid," *Chem. & Mol. Biol. of the Intercellular Matrix* 2, E. A. Balazs (1970) by T. C. Laurent, pp. 703–732.

"Biosynthesis of Hyaluronic Acid by Streptococcus," *The Journal of Biological Chemistry*, vol. 254, No. 14, issued Jul. 25, 1979, pp. 6252–6261, by Sugahara et al.

"The Isolation and Characterization of Hyaluronic Acid from Pasteurella Multocida," *Carbohydrate Research*, 14 (1970), 272–276 by J. A. Cifonelli.

"Streptococcal Bacteriophage 12/12–Borne Hyaluronidase and its Characterization as a Lyase (EC 4.2.99.1) by Means of Streptococcal Hyaluronic Acid and Purified Bacteriophage Suspensions," *Acta Path. Microbiol. Scand.* Sect. B, 84: 145–153, 1976 by H. Niemann et al.

"A Serologically Inactive Polysaccharide elaborated by Mucoid Strains of Group A Hemolytic Streptociccus," *Journal of Biological Chemistry*, (1937), pp. 61, 68, and 69, by Forrest E. Kendall et al.

"III. Hyaluronic Acid," *Mucopolysaccharides of Higher Animals in the Carbohydrates*, vol. IIB. (1970), 2nd Ed. by R. W. Jeanloz, pp. 592–597.

"Sequential Hydrolysis of Hyaluronate by B-glucuronidas and B-N-acetylhexosaminidase," *Biochem. J.* (1981) 197, 275–282, by Maria O. Longas et al.

"Comparison of Media and Culture Techniques for Detection of Streptococcus Pneumoniae in Respiratory Secretions," *Journal of Clinical Microbiology*, Dec. 1980, pp. 772–775 by T. C. Wu et al.

"Hyaluronic Acid Capsule: Strategy for Oxygen Resistance in Group A Streptococci," *Journal of Bacteriology*, Dec. 1979, pp. 1090–1097 by P. Patrick Cleary.

"Carbon Dioxide Control of Lag Period and Growth of Streptococcus Sanguis," *Journal of Bacteriology*, vol. 117, No. 2, Feb. 1974, pp. 652–659 by Roy Repaske et al.

"The Biosynthesis of Hyaluronic Acid by Streptococcus," *The Journal of Biological Chemistry*, vol. 244, No. 2, Jan. 25, 1969, pp. 236–246 by A. C. Stoolmiller et al.

"Hyaluronic Acid in Plants of Microorganisms," bibliography prepared by *Bibliographic Retrieval Services, Inc.* (dated 4/03/82).

"Hyaluronidase Bibliography" by *Worthington Biochemical Corporation*, Freehold, N.J. (through 1970).

"Rapid Purification of Interferon with Millipore Pellicon Cassette Systems, *Technical Service Brief*, Millipore Corporation, Bedford, Mass., Cat. No. TS062, 1981.

"Pellicon Cassette System—Assembly, Operation, Maintenance Instructions," Millipore Corporation, Bedford, Mass., (brochure) Cat. No. OM029, Part No. 11041, 3/1981.

HYALURONIC ACID FROM BACTERIAL CULTURE

BACKGROUND OF THE INVENTION

Hyaluronic acid is a mucoid polysaccharide of biological origin. The sodium salt, sodium hyaluronate, in buffered physiological saline solution, has found significant use as a vitreous replacement in optical surgery and in other medical applications. Some of these applications are described in U.S. Pat. Nos. 4,141,973 and 4,328,803. For such medical purposes, a pyrogen-free, highly purified sodium hyaluronate having a molecular weight in excess of 750,000 has heretofore been used. A commercial product known as HEALON TM, manufactured by Pharmacia, Inc., Piscataway, N.J., is a one-percent solution of sodium hyaluronate sold for such purposes. For example, dilute HEALON TM solution (0.1–0.2% sodium hyaluronate) has been reported to be useful as an eye drop for the treatment of patients with keratitis sicca syndrome.

Hyaluronic acid has also been used as an ingredient for in vitro culture of leprosy baccili and as a component for cosmetic formulations. Cosmetic formulations, which are described in U.S. Pat. No. 4,303,676, include both a low molecular weight fraction (about 10–50,000) and a higher molecular weight fraction (in excess of $1 \times 10^6$).

The source of hyaluronic acid for all of the foregoing uses have been rooster combs, human umbilical cords or other vertebrate tissue. Extraction and purification of hyaluronic acid from such tissue is a relatively complex process which results in a very expensive product.

Hyaluronic acid can be produced by Group A and C strains of Streptococcus bacteria. One use reported for the bacterial product appears to be as a reagent for determination of anti-streptococcal hyaluronidase in human serum samples, Kjems and Lebech, Acta Path. microbiol scand., Section B, 84: 162–164 (1976). In that paper, the authors describe a defined media for growing Group A streptococci and isolating hyaluronic acid, reporting a yield of 0.3 grams per liter of culture broth. However, hyaluronic acid produced by bacteria has not found substantial use because it is of a low molecular weight range.

BRIEF DESCRIPTION OF THE INVENTION

The present invention provides hyaluronic acid from bacterial sources of a preferred higher molecular weight range than is reported in the prior art as being obtained from bacterial sources. It also provides a method for producing hyaluronic acid from bacterial sources in much higher yields than has previously been reported. The method additionally produces hyaluronic acid which has a purity comparable to or better than any presently available for medical applications. Although the hyaluronic acid produced by the present method typically has an average molecular weight of about 55,000, it has potentially significant use as an eye drop ingredient and as an ingredient of cosmetic formulations. The high yield, high purity and low cost of the hyaluronic acid produced by the inventive method also permits it to be used in ways not previously described or contemplated for hyaluronic acid obtained from mammalian or low yield bacterial sources. For instance, hyaluronic acid might be used in food preparations as a humectant, in other applications as a lubricant, and in post-surgical applications for reducing complications due to fibrotic response and/or adhesion formation. The material might also be used in tertiary oil recovery as a substitute for polyacrylamide, similar synthetic polymers or biologically-produced polymers.

The inventive method in its preferred form comprises growing a culture of a hyaluronic acid-producing streptococcus strain under anaerobic conditions in a $CO_2$-enriched growth medium, which includes those raw materials necessary for the production of the hyaluronic acid by the bacteria, preferably although not necessarily killing the bacteria, separating the bacteria from the growth medium and isolating the hyaluronic acid. Preferably, growth is accomplished by fermentation in a broth culture. Other growth techniques and media may be used. For example, an agar culture may be used. Hence, the term "growth medium" herein is to be taken broadly as meaning liquid or solid media or combinations thereof and other types of growth in addition to fermentation, as are all well known in the art.

Although the preferred form of the invention contemplates the growth of bacteria directly in the culture medium in which the hyaluronic acid is to be produced, it is also possible to grow the bacteria in other growth media, separate the bacteria from the medium, resuspend the bacteria in a buffered suspension medium or distilled water and add the appropriate raw materials to the suspension for the production of the hyaluronic acid by the already grown bacteria. This is considered to be an art equivalent to the preferred method and merely involves the use of a resting cell suspension. Consequently, such terminology herein as "growing a culture" and the like is to be taken as including both approaches within its purview.

Unlike prior methods of hyaluronic acid production, endotoxins can be excluded from the system initially by filtering all ingredients through a 10,000 (10K) nominal molecular weight limit (NMWL) cutoff filter, such as the Millipore ® Pellicon ® cassette tangential flow filtration system, prior to inoculation and subsequently maintaining pyrogen-free anaerobic growth conditions.

DETAILED DESCRIPTION OF THE INVENTION

In the preferred embodiment of the present invention, a semi-defined growth medium such as the following is used:

1. Casein hydrolysate, enzymatic: 20.0 g
2. Potassium chloride: 3.0 g
3. Sodium phosphate, dibasic: 2.8 g
4. Magnesium sulfate (7H$_2$O): 0.5 g
5. Calcium chloride (2H$_2$O): 10.0 mg
6. Glucose: 20.0 g
7. Vitamin solutions:
   (a) d-Biotin: 1.0 mg
   (b) D-Calcium Pantothenate: 1.0 mg
   (c) Choline chloride: 1.0 mg
   (d) Folic acid: 1.0 mg
   (e) i-Inositol: 2.0 mg
   (f) Nicotinamide: 1.0 mg
   (g) Pyridoxal HCl: 1.0 mg
   (h) Riboflavin: 0.1 mg
   (i) Thiamine HCl: 1.0 mg The medium is made up to one liter with reverse osmosis pyrogen-free water. Of course, other growth media suitable for this purpose may also be used.

A 100 ml culture of Streptococcus pyogenes type is grown anaerobically for six hours in the medium at 37±1° C. The other hyaluronic acid-producing bacteria referred to hereinabove may be used, but the type 18 is preferred. Five liters of the same medium are inoculated with this six-hour culture and grown to a high visible density, preferably to at least $2 \times 10^8$ cells per ml and typically to $5 \times 10^8$ cells per ml. The five liter inoculum is then used to inoculate 160 liters of medium in a 200 liter fermentor to begin a production run.

During the production run, the culture is grown with continuous agitation while infusing $CO_2$ gas at a rate of flow sufficient to maintain a dissolved level of $CO_2$ as determined by a $CO_2$ monitoring probe. A 5–10% level of dissolved $CO_2$ is preferred. The gas is preferably infused as an $N_2/CO_2$ mixture. An 85/15 ratio is preferred, but not critical. The $CO_2$ level may range up to about 50%±10%. The gas is filter-sterilized as it is introduced into the growth chamber. Temperature is preferably controlled at about 37±1° C. The pH is preferably controlled to a substantially constant value ±0.1 within the range of about 6.5 to 7.5 by monitoring with a pH probe/controller and by the addition of KOH as called for by the controller. Fermentation is considered complete when the pH of the culture stops dropping (no more KOH is called for to maintain pH within the set limitation), or when the cell density reaches the high visible density, typically $1-5 \times 10^9$ cells per ml. At this point the fermentation is terminated by the addition of 100% saturated solution of aqueous trichloroacetic acid to make the fermentation mixture up to a final trichloroacetic acid concentration of about 5%. This may vary.

The addition of trichloroacetic acid to the fermentation broth not only terminates growth by killing the bacteria, but also makes separation of the cells from the broth substantially easier by contributing to flocculation of the cells. The mixture without trichloroacetic acid is very difficult to separate without causing severe disruption of the integrity of both components. Microorganisms and the polysaccharide ie., the hyaluronic acid, do not readily separate by centrifugation or filtration without the trichloroacetic acid addition. Thus, while it is possible to terminate growth of the culture by other means, for instance heat treatment, trichloroacetic acid treatment has the advantage of facilitating subsequent separation of the hyaluronic acid.

The fermentation mixture is pumped from the fermenter through a 0.22 micrometer pore-size Durapore ® filtration cassette using the aforementioned Millipore ® tangential flow filtration system. This step concentrates the cells from 160 liters to approximately five liters. The filtrate is retained and diafiltered against greater than 10 mega-ohm conductivity reverse osmosis water using a 30,000 nominal molecular weight cut-off Millipore ® Pellicon ® cassette system until the filtrate, which is continuously discarded, reaches a conductivity of approximately 0.5 mega-ohms. Diafiltering is a powered dialysis technique, such as is disclosed in Catalog Number OM029, March 1981, entitled *Pellicon ® Cassette System,* of Millipore Corporation, Bedford, Mass. 01730, as opposed to conventional passive dialysis techniques. The hyaluronic acid is then concentrated by continuing the filtration process without further input of water.

The concentrate is then treated with reagent grade ethanol, preferably in a 3:1 ratio. Other alcohols, acetone, chloroform or other organic solvents as well as certain organic salts such as CETAB, a mixed trimethylammonium bromide, may be used to precipitate the hyaluronic acid or sodium hyaluronate from the aqueous solution. This should be done without any mixing other than occurs in the act of pumping the hyaluronic acid into the solvent. Stirring during alcohol treatment has been found to reduce the process yield of hyaluronic acid. The precipitate at this stage can be stored indefinitely in the dark at 4° C.

As is seen from the procedure described, a unique approach is found in the isolation of the hyaluronic acid from the broth by a two-step process in which a molecular weight separation step is carried out by diafiltration to separate the acid from substantially all of the lower molecular weight components of the broth, and then the acid is separated from any remaining broth constituents by precipitation.

The precipitated hyaluronic acid can be dewatered (removal of the bulk of the water/alcohol solution) by a number of conventional techniques and then resuspended in reverse osmosis water or a 0.15M NaCl solution. The resuspended material is then lyophilized (freeze-dried), spray-dried, vacuum-dried or diafiltered to remove the last traces of alcohol. Further purification is performed by making a 0.05M Borate buffer solution, pH 8.0, with approximately a 10 mg/ml sodium hyaluronate concentration. 0.32% CETAB, is then added to the solution and the mixture stirred at 4° C. overnight to yield a precipitate, sodium hyaluronate. Other precipitating agents may be used, such as cetyl pyridium chloride or related salts. The precipitate is recovered by coarse filtration and resuspended in a 1M NaCl solution made with reverse osmosis water. The resuspended hyaluronic acid is then diafiltered and concentrated as above. The resultant hyaluronic acid can then be filter-sterilized and used or converted to sodium hyaluronate and then be filter-sterilized and used.

Conventional dewatering techniques include pressing, centrifugation, chemical addition and the like. The particular technique selected will depend on the subsequent intended use of the precipitate.

If a medical grade pyrogen-free product is desired, a pyrogen-free filtered growth medium is used and all operations of the process, including the isolation and processing of the hyaluronic acid/sodium hyaluronate are performed under conditions of a class 100 clean room using pyrogen-free containers. If the material is to be used only for chemical grade application, the cleanliness of the room and collection containers is not critical with respect to pyrogens.

The inventive method which emphasizes growing cells under non-aerated conditions prevents the streptococcus from producing its normal complement of end products, primarily the pyrogenic exotoxins for which the microbe is so well known. The described growth conditions also give a much higher yield of hyaluronic acid than has been previously reported. A minimum of 2 grams of hyaluronic acid per liter of culture broth has been obtained using the preferred cell growth and isolation conditions described above. The high yield under the non-aerated conditions is unexpected since one of the proposed functions of hyaluronic acid is thought to be that of providing an oxygen barrier for the cell. Thus, its production would only be expected to be maximized under conditions of exposure to oxygen.

The hyaluronic acid/sodium hyaluronate prepared as described has an average molecular weight of about 55,000± about 20% within a molecular weight range of from about 10,000–2,000,000 as determined by gel filtration or by quasi-elastic light scattering techniques.

These techniques are well known as are the variations in measurement and the results obtained with them due to biological variation. The product also has a protein content of between 0.3% and 0.03% depending on method of analysis. The UV absorption of the 0.1% solution is 0.314 at 260 nm and 0.169 at 280 nm. Viscosity of a 1% solution is approximately 300 centistokes.

A 0.5–1.5 percent solution of the pyrogen-free NaHy produced by the inventive method may be used as an eye drop composition in place of the very dilute solutions of high molecular weight rooster comb derived hyaluronic acid presently used for treatment of keratitis sicca.

Other hyaluronic acid-producing streptococci in the Group A and Group C strains may be used in the invention. Additionally, variations in the growth medium and conditions of growth, as well as variations in the isolation procedures, may be made without departing from the invention which is set forth in the following claims.

What is claimed is:

1. A method of producing hyaluronic acid comprising:
   fermenting a broth culture of hyaluronic acid-producing streptococcus bacteria in a growth medium under $CO_2$-enriched anaerobic conditions;
   separating the bacterial cells from the resulting broth; and
   isolating the hyaluronic acid from the remaining constituents of the broth by separating the acid and those broth consituents of similar or higher molecular weight and then separating the acid from those similar broth constituents by precipitation.

2. A method as in claim 1 wherein the growth medium is made pyrogen-free prior to inoculation by filtration thereof through a 10,000 molecular weight cutoff filter.

3. A method as in claim 1 wherein the bacterial cell separation step includes first adding trichloroacetic acid to the broth.

4. A method as in claim 3 wherein the trichloroacetic acid is added to make the fermentation mixture up to a final concentration of 5–6%.

5. A method as in claim 3 wherein the growth of the bacteria is terminated by said addition of trichloroacetic acid.

6. The method of claim 1 wherein the precipitation is accomplished by adding the hyaluronic acid and the remaining broth constituents to ethanol without substantial mixing.

7. The method of claim 1 wherein isolation is accomplished by separating the broth from the cells, diafiltering the broth and precipitating the acid from solution by adding the solution to an organic solvent without substantial mixing.

8. A method as in claim 1 wherein the fermentation step includes controlling the pH at a substantially constant value $\pm 0.1$ within the range of 6.5–7.5 and the temperature to $37 \pm 1°$ C. throughout fermentation.

9. A method as in claim 8 wherein the pH is controlled by the automatic addition of base with a pH probe/controller.

10. A method as in claim 1 wherein the dissolved $CO_2$ is maintained at a concentration of about 5–10%.

11. A method as in claim 1 wherein the bacteria is grown to a density of greater than $2 \times 10^8$ cells per ml before termination of growth.

12. The method of claim 1 wherein the baceria are *Streptococcus pyogenes* type 18.

13. A method as in claim 1 carried out by filtering the growth medium through a 10,000 molecular weight cutoff filter prior to inoculation with the bacteria culture and performing the remaining steps under conditions of a class 100 clean room using pyrogen-free containers.

14. A method as in claim 13 further comprising: refining the isolated hyaluronic acid by dissolution thereof in a mildly basic buffered solution, precipitation of sodium hyaluronate with a mixed alkyl trimethylammonium bromide, resuspending the precipitate in dilute sodium chloride solution and reprecipitating it as acid by adding it to ethanol without stirring.

15. In the method of producing hyaluronic acid involving production of same by streptococcus bacteria, the improvement comprising isolating the acid from the broth in which the bacteria grows by separating the acid and those broth constituents of similar or higher molecular weight from the liquid and then separating the acid from those similar broth constituents by precipitation, and wherein the precipitation is accomplished by adding the acid and the remaining broth constituents to ethanol without mixing.

16. The method of claim 15 wherein the bacteria are *Streptococcus pyogenes* type 18.

17. The method of claim 15 wherein isolation is accomplished by separating the broth from the bacteria, diafiltering the broth and precipitating the acid from resulting solution by adding the solution to an organic solvent without any substantial mixing.

18. In the method of producing hyaluronic acid involving production of same by streptococcus bacteria, the improvement involving the maintenance of $CO_2$-enriched anerobic conditions in the environment of the bacteria growth medium.

19. A method of producing hyaluronic acid comprising:
   growing a culture of hyaluronic acid-producing streptococcus bacteria in a growth medium under $CO_2$-enriched anaerobic conditions;
   forming a liquid suspension of the bacteria and its by-products in the case where the formation of such a suspension is not inherent in the growth method being used;
   separating the bacterial cells from the suspension; and
   isolating the hyaluronic acid from the constituents of the remaining liquid by separating the acid and those broth constituents of similar or higher molecular weight and then separating the acid from those similar broth constituents by precipitation.

20. A method as in claim 19 wherein the growth step includes controlling the pH at a substantially constant $\pm 0.1$ value within the range of 6.5–7.5 and the temperature to $37 \pm 1°$ C. throughout fermentation.

21. A method as in claim 19 wherein the pH is controlled by the automatic addition of base with a pH probe/controller.

22. A method of producing hyaluronic acid comprising:
   growing a culture of acid-producing streptococcus bacteria under $CO_2$-enriched anaerobic conditions on a solid growth medium;
   forming a liquid suspension of the bacteria and its by-products to separate same from the solid medium,
   separating the bacterial cells from the suspension; and
   isolating the hyaluronic acid from the constituents of the remaining liquid by separating the acid and those liquid constituents of similar or higher molecular weight from the liquid suspension and then separating the acid from those similar constituents.

23. The method of claim 22 wherein the precipitation is accomplished by adding the hyaluronic acid and the remaining constituents to ethanol without substantial mixing.

24. A method as in claim 22 wherein the fermentation step includes controlling the pH at a substantially constant value ±0.1 within the range of 6.5–7.5 and the temperature to 37±1° C. throughout fermentation.

25. A method as in claim 22 wherein the dissolved $CO_2$ is maintained at a concentration of about 5–10%.

26. A method as in claim 22 wherein the bacteria is grown to a density of greater than $2 \times 10^8$ cells per ml before termination of growth.

27. A method as in claim 22 further comprising: refining the isolated hyaluronic acid by dissolution thereof in a mildly buffered solution, precipitation of sodium haluronate with a mixed alkyl trimethylammonium bromide, resuspending the precipitate in dilute sodium chloride solution and reprecipitating it as acid by adding it to ethanol without stirring.

28. A method of producing hyaluronic acid comprising:
   providing hyaluronic acid-producing streptococcus bacteria;
   combining the bacteria with a growth medium whereby the bacteria produces by-products including hyaluronic acid;
   maintaining $CO_2$-enriched anaerobic conditions in the environment of the growth medium;
   forming a liquid suspension of the bacteria and its by-products in the case where the formation of such a suspension is not inherent in the growth method and medium being used;
   separating the bacteria from the suspension; and
   isolating the hyaluronic acid from the constituents of the remaining liquid by separating the acid and those liquid constituents of similar or higher molecular weight from the liquid suspension and then separating the acid from those similar constituents.

29. The method of claim 28 wherein the bacteria is initially provided in a resting suspension.

30. The method of claim 28 wherein the bacteria is *Streptococcus pyogenes* type 18.

* * * * *

UNITED STATES PATENT AND TRADEMARK OFFICE
CERTIFICATE OF CORRECTION

PATENT NO. : 4,517,295

DATED : May 14, 1985

INVENTOR(S) : James W. Bracke and Kipling Thacker

It is certified that error appears in the above–identified patent and that said Letters Patent are hereby corrected as shown below:

Column 3, lines 15, 16, "The $CO_2$ level may range up to about 50% $\pm$ 10%." should be deleted.

Signed and Sealed this

Twelfth Day of August 1986

[SEAL]

Attest:

Attesting Officer

DONALD J. QUIGG

Commissioner of Patents and Trademarks